(12) United States Patent
Legrand et al.

(10) Patent No.: US 8,966,772 B2
(45) Date of Patent: Mar. 3, 2015

(54) SURGICAL BLADE ASSEMBLY

(75) Inventors: Bernard P. Legrand, Conches (CH); Marc Detry, Ayze (FR)

(73) Assignee: Zimmer Surgical SA, Geneva (CH)

( * ) Notice: Subject to any disclaimer, the term of this patent is extended or adjusted under 35 U.S.C. 154(b) by 0 days.

(21) Appl. No.: 13/544,110

(22) Filed: Jul. 9, 2012

(65) Prior Publication Data
US 2012/0289963 A1 Nov. 15, 2012

Related U.S. Application Data

(63) Continuation of application No. PCT/EP2011/050236, filed on Jan. 10, 2011.

(60) Provisional application No. 61/293,772, filed on Jan. 11, 2010.

(51) Int. Cl.
*B27B 5/29* (2006.01)
*B26B 19/12* (2006.01)
(Continued)

(52) U.S. Cl.
CPC .............. *B27B 19/006* (2013.01); *A61B 17/14* (2013.01); *A61B 17/148* (2013.01); *B27B 5/32* (2013.01); *B27B 19/008* (2013.01)
USPC .............. 30/166.3; 606/176; 606/82; 30/208; 30/337

(58) Field of Classification Search
CPC .... A61B 17/14; A61B 17/148; A61B 17/141; B27B 19/006; B27B 5/32
USPC ........ 30/166.3, 374, 208–222, 337, 339, 340, 30/342, 334, 343, 500; 606/167, 176–178, 606/79, 82
See application file for complete search history.

(56) References Cited

U.S. PATENT DOCUMENTS 1,754,650 A * 4/1930 Seaholm .......................... 30/337
4,036,236 A 7/1977 Rhodes, Jr.
(Continued)

FOREIGN PATENT DOCUMENTS

| DE | 4036904 | * | 5/1992 |
| DE | 10164081 | | 7/2003 |
| EP | 1974881 | | 10/2008 |

OTHER PUBLICATIONS

Collins English Dictionary, "recess" definition, available at http://www.collinsdictionary.com/dictionary/english/recess.*
(Continued)

*Primary Examiner* — Sean Michalski
*Assistant Examiner* — Jonathan G Riley
(74) *Attorney, Agent, or Firm* — Seager, Tufte & Wickhem, LLC

(57) ABSTRACT

A surgical blade assembly for use with a driver includes a blade with a distal cutting portion, and a proximal end has a first dimension which is less than what is applicable for use with a specific driver head. An insert is affixed to the blade proximal end and, when affixed to the blade proximal end, is configured to enable the blade for use with the driver head. A surgical cutting tool includes such a surgical blade assembly and a driver head receiving the blade assembly. A surgical cutting tool kit includes a driver with a head for receiving the blade assembly, and a plurality of such surgical blade assemblies for use with the driver, wherein the blades have different thicknesses (a) and/or widths and the corresponding inserts are configured such that the proximal ends of the surgical blade assemblies all include at least one same constant dimension (b).

10 Claims, 4 Drawing Sheets

(51) Int. Cl.
*B26B 1/00* (2006.01)
*A61B 17/00* (2006.01)
*A61B 17/14* (2006.01)
*B27B 19/00* (2006.01)
*B27B 5/32* (2006.01)

(56) References Cited

U.S. PATENT DOCUMENTS

| | | | | |
|---|---|---|---|---|
| 4,617,930 | A | * | 10/1986 | Saunders ........................ 606/82 |
| 5,178,626 | A | * | 1/1993 | Pappas ......................... 606/178 |
| 5,263,972 | A | | 11/1993 | Evans et al. |
| 5,439,472 | A | * | 8/1995 | Evans et al. .................. 606/176 |
| D385,163 | S | * | 10/1997 | Hutchins et al. ................. D8/20 |
| 5,735,866 | A | * | 4/1998 | Adams et al. ................. 606/178 |
| 6,113,618 | A | * | 9/2000 | Nic ............................... 606/176 |
| D492,412 | S | * | 6/2004 | Desoutter et al. ............ D24/146 |
| 7,691,106 | B2 | * | 4/2010 | Schenberger et al. .......... 606/82 |
| 2008/0027449 | A1 | | 1/2008 | Gundlapalli et al. |
| 2009/0312762 | A1 | * | 12/2009 | Boykin .............................. 606/82 |
| 2010/0292701 | A1 | | 11/2010 | Fisher et al. |

OTHER PUBLICATIONS

International Search Report and Written Opinion for PCT Patent App. No. PCT/EP2011/050236 (Oct. 19, 2011).
International Preliminary Report on Patentability for PCT Patent App. No. PCT/EP2011/050236 (Jul. 11, 2012).

* cited by examiner

SURGICAL BLADE ASSEMBLY

This application is a Continuation of, and claims priority under 35 U.S.C. §120 to, International Application No. PCT/EP2011/050236, filed 10 Jan. 2011, and claims priority therethrough under 35 U.S.C. §§119, 365 to U.S. Provisional App. No. 61/293,772, filed 11 Jan. 2010, the entireties of which are incorporated by reference herein.

BACKGROUND

1. Field of Endeavor

The present disclosure relates to a surgical blade assembly and to a surgical cutting system. The present disclosure relates in particular to a surgical saw blade assembly for use with a powered surgical driver and to a surgical cutting tool for cutting bones or other tissues.

2. Brief Description of the Related Art

Powered surgical saws are powered tools that surgeons employ for performing certain surgical procedures that include cutting bones and/or other tissues. A powered surgical saw typically includes a handpiece, or driver, in which is housed a motor, for example an electrically or pneumatically driven motor. The motor is attached, for example through a drive shaft, to a head of the driver, which is adapted to removably receive a surgical saw blade. The actuation of the motor causes an oscillating movement of the head and of the attached saw blade. The movement of the saw blade is what gives the blade the power to cut through the tissue it is employed to separate. Powered surgical saws are able to cut through both hard and soft tissue much faster and with greater accuracy than manually operated saws. Powered surgical saws are furthermore able to perform specific cuts that manually operated saws are unable to perform. Also, the physical effort a surgeon has to employ to operate a powered surgical saw is much less than that used when cutting tissue with a manual saw.

Surgical saw blades for use with a powered surgical saw typically have a body with a proximal end, also referred to as the base, that is designed to sit in a slot or opening formed in the driver's head, and a distal end with a cutting portion. The base, or proximal end, is designed to tightly fit in the driver's head in all degrees of freedom in order to remain stable despite the vibrations and pressure it is submitted to when used. The cutting portion usually includes teeth adapted to a particular cutting action. The teeth are usually either fluted or bent, depending on the thickness of the blade and its intended use. The body of the blade is preferably rigid enough for providing a stable and stiff connection between the blade's cutting portion and the driver's head, thereby allowing an accurate cutting action. The length of the body furthermore determines the stroke of the cut, since the amplitude of the driver head's oscillations is constant, independently of the blade being used.

On some drivers, the blade is, for example, attached to the head with the help of bolts and nuts, or other similar locking devices, that hold two coupling members of the head together, between which the surgical saw blade is clamped. Such locking mechanisms can be configured to allow the use of saw blades of different thicknesses on a same head. A drawback of such locking mechanisms, however, is that they require the use of a tool, typically of a wrench, for locking the bolts and/or nuts and thus for securely attaching the blade to the driver's head. This makes replacing saw blades, which often occurs during surgery, a relatively complicated and long task. A further drawback for such a tool is the need to manipulate the head in order to lock the blade in place that may be time consuming and tough to do while using protective gloves.

Other powered surgical saws have heads with tool-less locking mechanisms for coupling the saw blades to the drivers. These mechanisms often require the depression of a button, the rotation or a lever, or some sort of spring loaded device for holding the head coupling members in position so that they lock the saw blade in place. The saw's proximal end for example includes one or more openings or slots in which one or more coupling members integral with the head seat in order to lock the blade to the head. The coupling member is displaced from the locked state to the release state, for example, by the depression of a button also built into the saw head. All one has to do is depress the button in order to move the coupling member to the unlocked state; the surgical personnel then remove one blade and insert a new blade. An advantage of these assemblies is that they eliminate the need to bring another tool, either a small wrench or a key, into the surgical suite. The elimination of this tool eliminates the need to have to sterilize it before an operation and the need to have to account for its presence.

U.S. Pat. No. 5,263,972, for example, describes a surgical powered saw with a tool-less locking mechanism for removably attaching a surgical saw blade to the saw head. The saw described in this document is able to receive blades of a range of thicknesses, wherein the blade's base or proximal end is chucked in a slot whose height can be significantly larger than the blade's thickness. When locked on the saw head, the blade is urged against the top of the slot by spring elements pushing on the blade's lower side. A drawback of this powered saw blade is that if the moment of the forces exerted on the blade's distal end during cutting operations is higher than the moment of the forces exerted on the blade by the spring elements, the saw blade will move in a plane perpendicular to the orientation of its cutting portion, which would greatly impair the accuracy of the cutting operation.

SUMMARY

One of numerous aspects of the present disclosure includes devices of the aforementioned kind providing alternatives to the art mentioned above, and more particularly which can overcome drawbacks thereof.

Another aspect includes a saw blade assembly allowing for the secure locking of saw blades of different thicknesses on a single driver head.

Another aspect of the present disclosure includes a saw blade assembly allowing for the easy locking of saw blades of various thicknesses on a single driver head.

Still another aspect of the present disclosure includes a surgical cutting system allowing for the easy and secure use of saw blades of different thicknesses on a single head.

Yet another aspect includes a surgical blade assembly for use with a driver for forming a surgical cutting tool, the surgical blade assembly comprising a blade having a proximal end and a distal end with a cutting portion, the proximal end having a first dimension which is less than what is applicable for use with the head of a specific driver, and an insert affixed to the proximal end of the blade, wherein the insert, when affixed to the proximal end of the blade, is configured to enable the blade for use with the head of the driver.

Another aspect includes a surgical cutting tool comprising such a surgical blade assembly and a driver comprising a head for receiving the blade assembly.

Yet another aspect includes a surgical cutting kit, comprising a driver with a head for receiving the blade assembly, and a plurality of such surgical blade assemblies for use with the driver, wherein the blades have different thicknesses and/or widths and the corresponding inserts are configured such that the proximal end of the plurality of surgical blade assemblies all comprise at least one same constant dimension.

Accordingly, an adaptor, also referred to as an "insert", is provided in combination with a saw blade. The insert may be made from any material capable of handling the forces/stresses/strains (together "forces") of the intended use, for example cutting, such forces when used with an electric or pneumatic powered driver when cutting tissues, for example, bone. Thus, such materials as plastics, reinforced/engineered plastics, carbon fiber, metals/metallic alloys, and the like, may be used. The inserts are in one exemplary embodiment configured to be attached with or used in combination with blades having different thicknesses. In some embodiments, the inserts are configured for example to enable different thicknesses of blades to be used with a head of a driver designed for use with a single blade thickness, or with those drivers which required adjustment. According to these embodiments, an insert is thus adapted for example to the thickness of a particular blade, in order to allow the use of this particular blade with the head unit of a driver having an opening whose dimensions are adapted for receiving blades of various thicknesses.

BRIEF DESCRIPTION OF THE DRAWINGS

The above and further advantages of the invention will be better understood by reference to the following description illustrated by the figures, where.

DETAILED DESCRIPTION OF EXEMPLARY EMBODIMENTS

Figure 1:
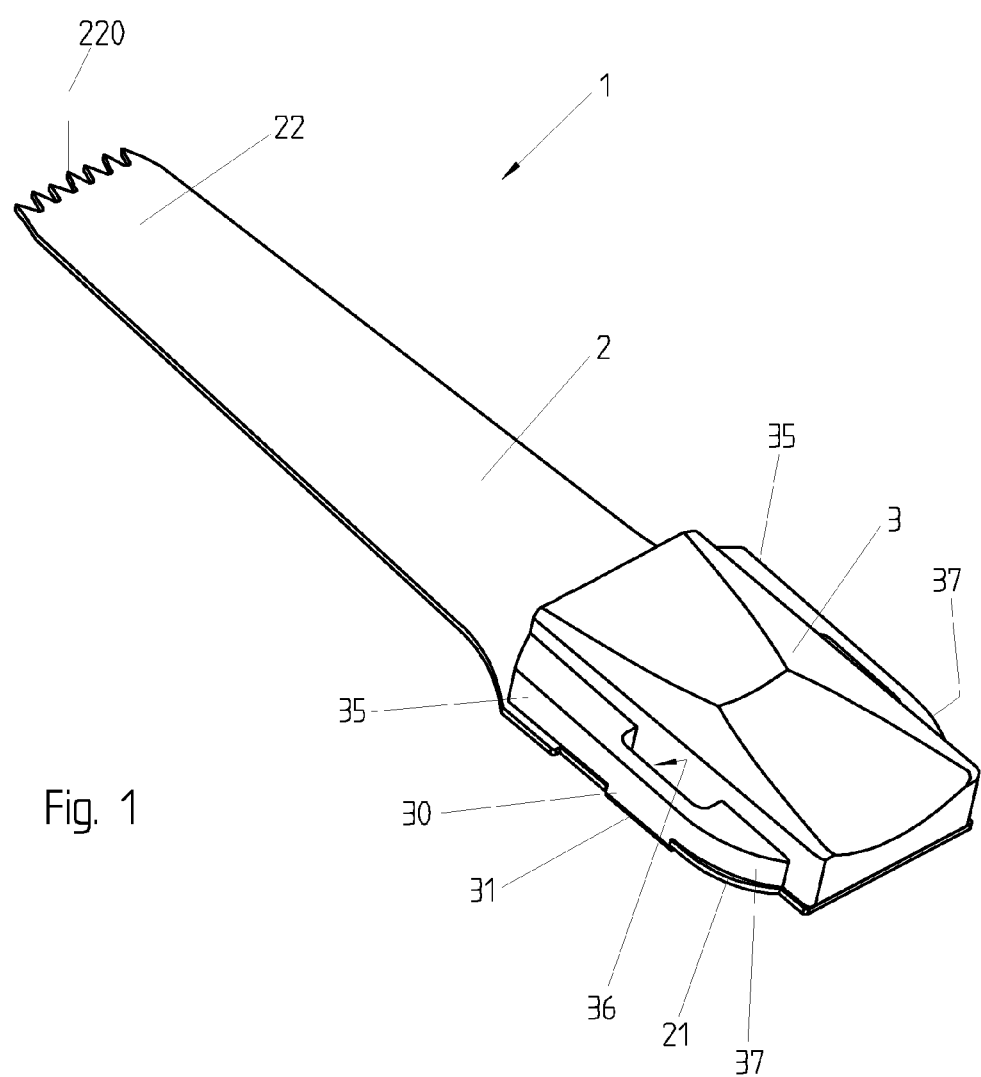
FIG. 1 is a perspective view of an illustrative, but not limiting, example of a blade assembly according to an exemplary embodiment.

FIG. 1 shows an example of a surgical blade assembly 1 according to an exemplary embodiment of the invention. The blade assembly 1 has a surgical blade 2 and an insert 3, also referred to as an adaptor.

The surgical blade assembly 1 is configured for its use in a surgical cutting tool having the blade assembly 1 and a driver, also referred to as a hand-piece. The driver, which is not represented in the figures, includes a head for receiving the surgical blade assembly 1. The driver may be a power driver housing a motor, for example an electrically or pneumatically driven motor that is attached, for example through a drive shaft, to the head of the driver. The actuation of the motor causes an oscillating movement of the head and thus of the attached surgical blade assembly 1. This movement of the surgical blade assembly 1 is what gives the blade 2 the power to cut through the bones and other tissue it is employed to separate.

The surgical blade 2 of the surgical blade assembly 1 is, for example, a flat and elongated saw blade with a proximal end 21, to which the insert 3 is affixed, and a distal end 22 with a cutting portion 220. The cutting portion 220 includes a number of teeth of different dimensions and shapes that are preferably adapted to a particular surgical intervention, for example for cutting particular bones or other tissues.

Figure 6:
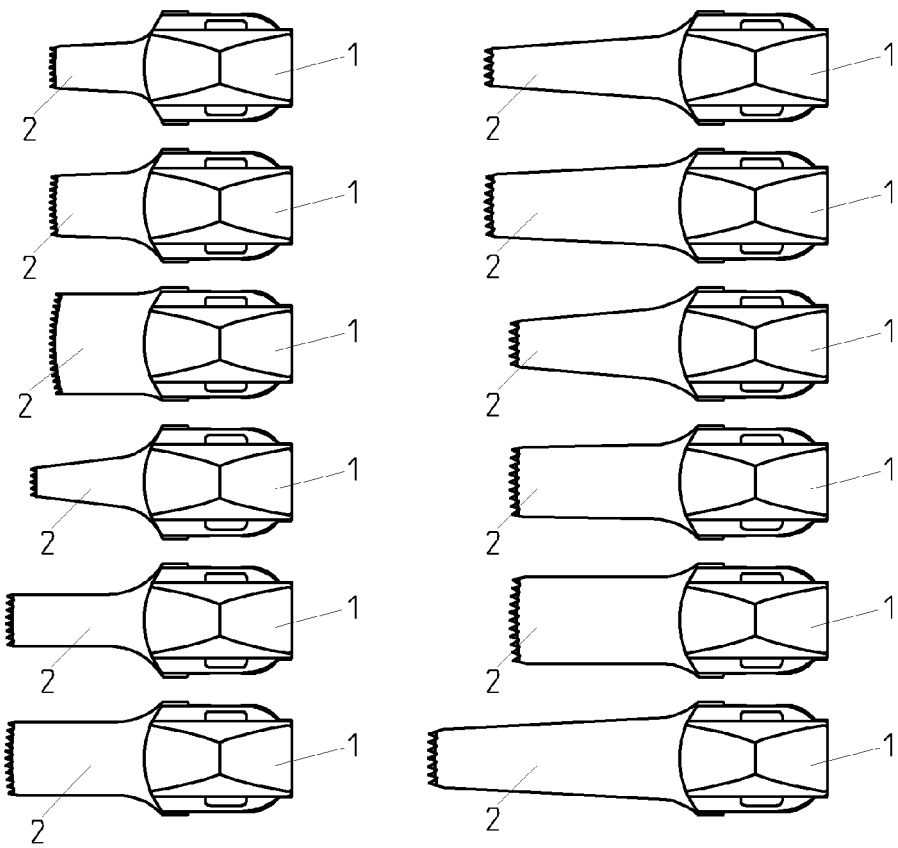
FIG. 6 shows an exemplary kit having a plurality of different blade assemblies for use with a same driver.

The surgical saw blade 2 illustrated in the figures is an illustrative, but not limiting, example of a surgical blade for use in the surgical blade assembly 1. Surgical saw blades useable within the scope of the invention may take a variety of forms in accordance with their particular cutting tasks, and may thus differ for example in their thicknesses and/or in the size and shape of their distal ends and cutting portions. This is illustrated for example in FIG. 6 that shows an example of a blade assembly kit having several saw blade assemblies 1 for use with a single driver, which is not represented in FIG. 6. In the illustrated example, each blade assembly 1 has a differently configured saw blade 2, the blades 2 having different lengths, different widths, differently configured cutting portions and/or different thicknesses.

According to an embodiment of the invention, the saw blade 2 is a flat saw blade, which is in specific embodiments made of stainless steel of relatively hard grade that is typically used for surgical saw blades. The saw blade 2 is, for example, made through embossing of a metal plate whose thickness typically ranges from 0.20 to 2.00 mm. Other dimensions are however possible within the spirit of the invention. In specific embodiments, the blade includes some reinforcement, for example longitudinal reinforcement ribs, for rigidifying the blade's body and/or some cut-out holes for reducing its weight.

For specific cutting operations, the width of the blade's distal end may have to be larger than that of the proximal end in order to accommodate a sufficiently long cutting portion. In corresponding embodiments, the saw blade may include a proximal end 21 having a width adapted to the dimensions of the driver's head, while the rest of the blade, which extends out of the driver head when the blade assembly is attached to the head, is wider.

According to one aspect of the invention, the insert 3, or adaptor, is shaped and dimensioned to allow the use of the surgical saw blade 2 in a surgical cutting tool configured for receiving saw blades and/or saw blade assemblies with one or more dimensions larger than the corresponding dimension or dimensions of the blade's proximal end 21. In particular, the insert 3 may be configured for allowing the correct insertion and tight locking of the surgical blade assembly 1 in a driver head with an opening or slot whose height is significantly larger than the thickness of the blade 2. According to the illustrated example, the general shape of the insert can be considered rectangular. Any other geometry may however be utilized as long as the functionality of the saw blade 2 is not impeded, and that it allows adequately affixing the blade assembly 1 to the driver, for example to a power driver.

The insert 3, in an exemplary embodiment, includes fastening devices, for example two or more clips 31, for securing/affixing it to the saw blade 2. According to the embodiment illustrated in the figures, the insert 3 for example has two clips 31 located on opposite sides of the insert 3, which extend from lateral guides 30 that arrange the insert 3 in a proper position relative to the saw blade 2. When the insert 3 is affixed, for example, to the upper side of the saw blade 2, the lateral guides 30 extend through corresponding notches in the lateral sides of the proximal end 21 of the saw blade 2 and the clips 31 rest against the lower side of the saw blade 2. The references to upper side and lower or bottom side are used for the purpose of simplicity and easy reference, with respect to the orientation of the saw blade assembly 1 as chosen in the figures. They may more generally be read as first and second sides, such that, e.g., the upper side may be referred to as a first side, and the lower or bottom side may be referred to as the second side, or vice versa, dependent on the reference system chosen. The clips 31 are made of any suitable material, for example plastic, metal, and the like. The clips 31 may be integral to the insert 3. In particular, if the insert 3 is made from a plastic material, the insert 3 and the clips 31 are for example molded as a single piece.

One or more other fastening devices and/or methods are however possible within the scope of the invention, in addition to clips and/or in place thereof, for securing/affixing the insert to the saw blade, including for example ultrasound welding, over-molding, centering pins, press-fits, gluing, and any other method and/or element that can enable the affixing of the insert to the saw blade.

Other alignment configurations are also possible within the scope of the invention for properly aligning the insert with the saw blade when the insert is affixed to the blade, including, for example, one or more pins extending from the lower side of the insert and extending through one or more corresponding openings in the proximal end of the saw blade, and/or any other suitable alignment structures. In variant embodiments, the alignment structures are, for example, separated from the fastening devices.

In the illustrated exemplary embodiment, the insert 3 further includes protruding nibs 35 that are configured for being received by corresponding recesses or chamfers in the head of a driver. The protruding nibs 35 are, for example, located on opposite sides of the insert 3 and extend parallel to the longitudinal axis of the saw blade assembly 1. The nibs 35 may more specifically rest on the upper side of the saw blade 2 when the insert 3 is affixed to the saw blade 2. The nibs 35 may furthermore have rounded corners 37 on their proximal ends in order to facilitate the insertion of the blade assembly 1 into the recesses of the driver's head.

According to the illustrated embodiment, the lateral guides 30 and the clips 31 extend from a flexible portion of the nibs 35, which allows the displacement, and in particular elastic displacement, of the guides 30 and thus of the clips 31 while the insert 3 is being clipped onto the saw blade 2. The flexible portion is for example formed through an opening 36 in the nib 35 that separates it from the rest of the insert 3 on a part of its length.

Inserts according to principles of the present invention may be configured to hold blades of various thicknesses, each insert being configured to hold a blade of a determined thickness.

Figure 2:
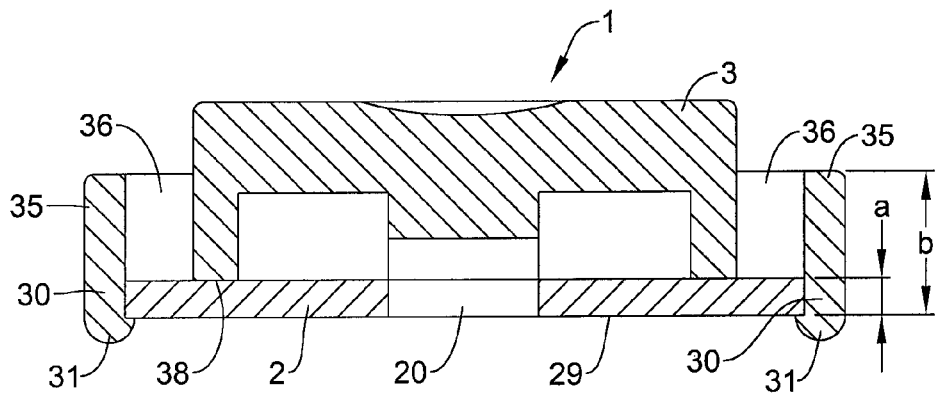
FIG. 2 is a cut view of the surgical blade assembly of FIG. 1.
Figure 2A:
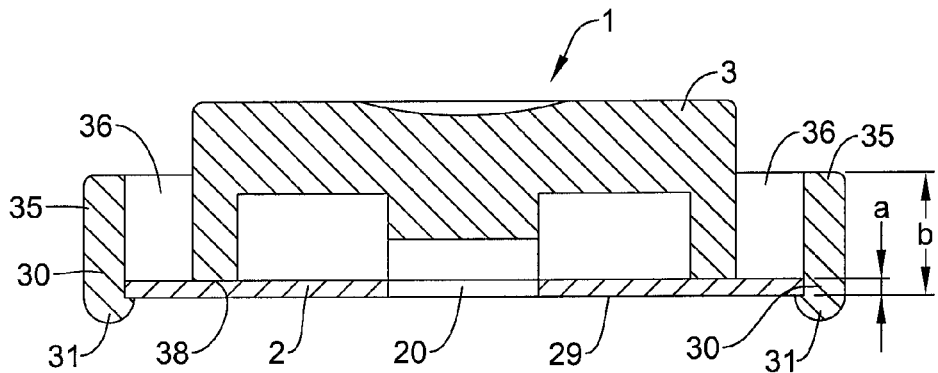
FIG. 2A is a cut view of another surgical blade assembly.

With reference to FIG. 2 and FIG. 2A, the distance between the lower side 38 of the insert 3 and the clip 31, which is referred to here as the height of the clip, is thus dimensioned to accommodate a saw blade 2 having a determined thickness "a" that varies. For example, FIG. 2 and FIG. 2A, illustrate a saw blade 2 having a thickness "a" different from one another. Further, in order to allow the use with a same head of saw blades 2 having different thicknesses "a", at least one external dimension of the blade assembly 1, for example the thickness of a particular part of the blade assembly 1, remains constant for all blade assemblies 1, independently of the thickness "a" of the particular saw blade 2.

In the illustrated embodiment, the constant dimension "b" corresponds to the distance from the upper side of the nib 35 to the lower side 29 of the saw blade 2. This constant dimension may vary along the nib 35, in which case it for example varies identically for all blade assemblies 1 configured for use with a same head. The constant dimension "b" is in more specific embodiments chosen to allow a tight fit of the saw blade 2 and nibs 35 in the corresponding recesses of the corresponding driver's head.

In specific embodiments, the width of the blade's proximal end 21 is the same for all blades 2 of all thicknesses, independently of the width of the rest of the blade and of the configuration of its cutting portion 220. The width of the proximal end 21 is, for example, dimensioned to tightly fit inside the driver's head when the corresponding blade assembly is locked onto the head. The blade 2 is then in tight and direct contact with the driver's head, which contributes to the secure and precise driving of the blade 2 when the driver is actuated and the head oscillates.

In other embodiments, blades having proximal ends, or bases, of different widths can be accommodated in a same driver's head in that the insert attached to the proximal end of each blade is dimensioned for having a constant width on at least part of their length, independently of the width of the proximal end. At least some of these inserts thus cover the lateral sides of the proximal end of their corresponding blade.

The insert can thus be configured to accommodate blades of different thicknesses and/or widths in a same driver's head by providing the corresponding blade assemblies with one or more constant dimensions of its proximal end, independently of the blade's thickness and/or width.

In the present disclosure, the expression "constant dimension" designates a dimension, measured on a particular reference spot, part and/or region of the blade assembly 1, which is the same on all blade assemblies 1 for use with a same driver, independently of the possibly different configuration and/or dimensions of the individual blades 2 included in these blades assemblies 1.

Figure 3:
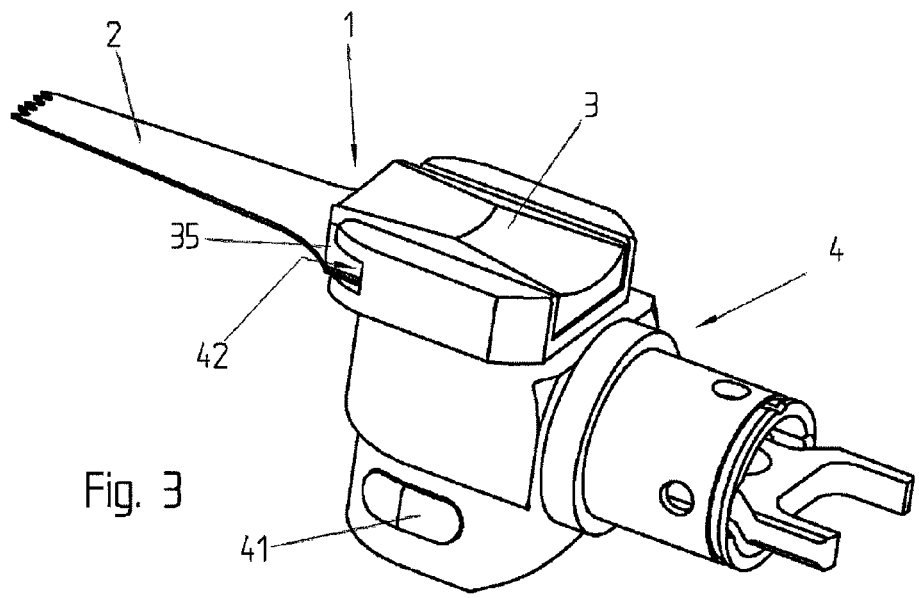
FIG. 3 is a perspective view of the blade assembly of FIG. 1 attached to a driver head.

FIG. 3 shows the blade assembly 1 according to an exemplary embodiment of the invention, attached to a head 4. The head 4 is configured to be part of a driver, e.g., of a motorized driver, which is not illustrated in the figures.

The blade assembly 1 is, for example, inserted with its proximal end into an opening of the head 4, which is at least partly delimited by the recesses 42. The nibs 35 slide inside the recesses 42 while the blade assembly 1 is pushed inside the opening along its longitudinal axis. Once the blade assembly 1 correctly sits on the head 4, in a position that allows the correct and safe use of the blade 2 for its intended task, the blade assembly 1 is locked on the head 4 through a locking mechanism, e.g., a tool-less locking mechanism, which may be integral to the head. The blade assembly 1 is, for example, locked on the head 4 through the saw blade 2, the insert 3 and/or a combination thereof. In one embodiment, the blade assembly 1 is removably locked onto to the head 4.

Figure 4:
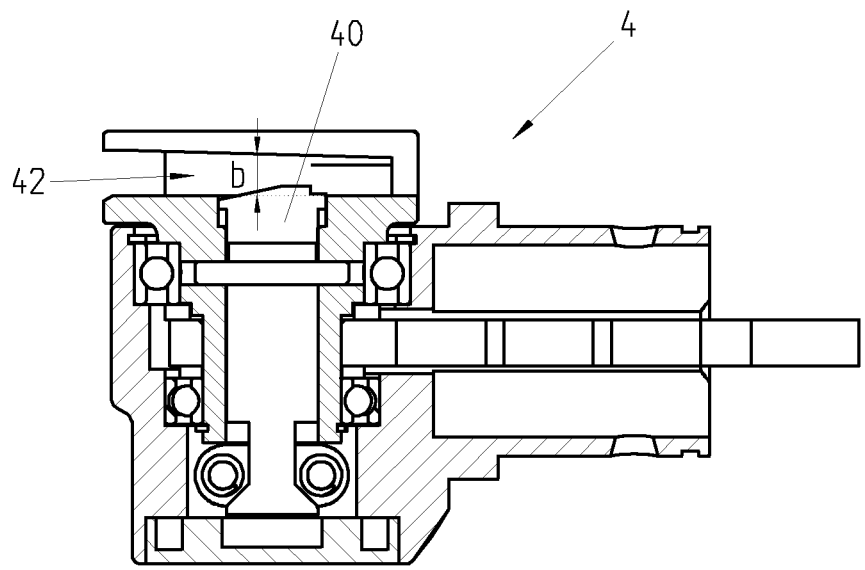
FIG. 4 is a longitudinal cut view of the driver head of FIG. 3.
Figure 5:
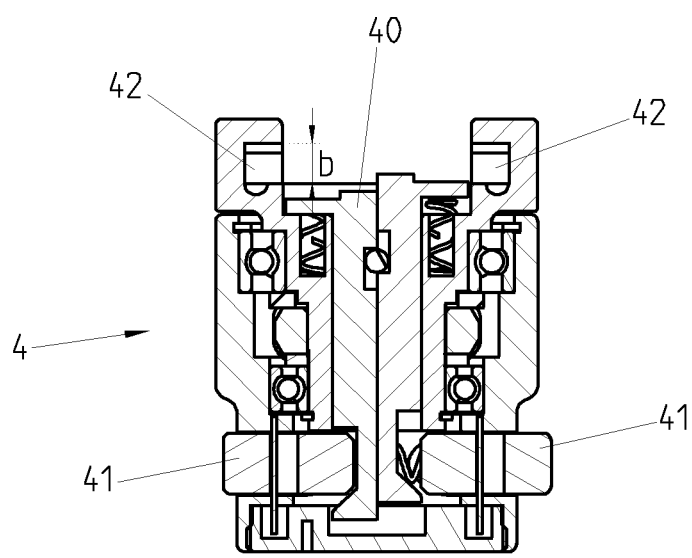
FIG. 5 is a lateral cut view of the driver head of FIG. 3.

With reference to FIGS. 4 and 5, the locking mechanism is, for example, a self-locking mechanism having a self locking pin 40 that extends into a corresponding aperture in the blade assembly when the blade assembly is locked on the head 4. In its locked position, the self locking pin 40 extends, for example, through an aperture 20 in the proximal end of the blade 2, visible in FIG. 2, whereas the locking pin 40, for example, extends into the saw blade 2 in order to provide adequate support. The extension of self-locking pin 40 in saw blade 2 ensures a safe locking of the blade assembly onto the head 4, the blade and the locking pin 40 being with advantage made of hard materials, for example metal alloys. The self-locking pin 40 may furthermore be dimensioned to tightly fit inside the blade's aperture, in order to avoid unwanted displacement of the blade assembly along its longitudinal axis relative to the head 4 when the blade assembly is locked on said head.

One or more buttons 41 may be provided, for example on the head 4 and/or on the driver body, for releasing and/or locking the locking mechanism. With reference to FIG. 5, the buttons 41 are, for example, located on the side of the head 4. According to an exemplary embodiment, the self-locking pin 40 has two parts, for example two halves, each part being actuated, in particular unlocked, by another button 41. In the chosen example, both buttons 41 must thus be pushed simultaneously in order to release the blade assembly from the head, thereby avoiding an undesired release of the blade assembly.

According to variant embodiments, the locking mechanism includes a plurality of pins or plates that move parallel and/or perpendicular to the plane of the blade, and/or a lever system that lifts a plate to create an opening to receive the proximal end of the blade assembly, wherein the lever is, for example, moved in a first direction to return the plate toward its original position establishing pressure to hold the blade assembly in place, and moved in an opposite direction to release the blade assembly, so that the blade assembly can be disengaged from the head of the driver.

Embodiments of the blade assembly 1 embodying principles of the present invention may be configured with two degrees of freedom being substantially controlled, and in some embodiments, completely controlled: lateral movement, e.g., along the horizontal plane of the blade 2, and the up/down or vertical movement, e.g., perpendicular to the plane of the blade 2. Laterally, the blade assembly 1 is in some embodiments fixed in a rigid manner with respect to the head 4, for example through an appropriate dimensioning of the width of the blade's proximal end 21, while vertical movement is supported/substantially controlled with the insert 3 in order to dampen the vibration of the blade for the operator. This control of the movements of the blade assembly 1 relative to the head 4 may in one specific embodiment be performed thanks to a tight fit of the blade assembly 1, in particular of the nibs 35 of the insert 3, inside the recesses or chamfers 42 whose height "b" correspond to the known and constant dimension "b" of the blade assembly 1.

As mentioned above, the dimension "b", which is the same on all blade assemblies configured for use with a same head, can vary along the length of the nibs 35. Dimension "b", for example, increases along the nibs 35 from the distal end towards the proximal end of the blade. This provides for an easier insertion and release of the blade assembly into and from the head's opening. The height of the recesses 42 then also similarly varies, such that the nibs are in tight contact with the inner surfaces of the recesses 42 on both sides and along their entire length when the head assembly is locked on the head 4.

It may prove advantageous if the material of the insert is chosen to be slightly softer and/or less wear resistant than that of the saw blade and of the head 4, in particular of the recesses 42, and the dimensions of the recesses are identical to or even slightly smaller than the dimensions of the nibs with the saw blade, such that the nibs are slightly compressed when the blade assembly is locked on the head 4, thereby providing for a complete control of the movements of the blade assembly, and thus of the blade, relative to the head 4.

The material of the insert 3, for example a plastic material, is hard enough for the insert 3 to resist the forces exerted on it when the saw blade assembly 1 is in use. In one specific embodiment, however, the material of the insert 3 is soft enough to wear out after one or more surgical operations performed with a same saw blade assembly, thereby making the particular saw blade assembly unsuitable for any further surgical use. This allows avoiding the extended use of a particular saw blade assembly, whose efficiency decreases with the wear of its cutting portion.

In variant embodiments, the insert 3 of the saw blade assembly 1 further functions to dampen vibrations caused by the driver during the operation. This is, for example, achieved by an appropriate choice of the insert's material and/or by an adapted configuration of the nibs 35 and/or of other parts of the insert 3 that are in direct contact with the head 4 when the blade assembly is attached to the head 4.

In variant embodiments, the insert 3 may include identifiers such as a radio-frequency-identification tag (RFID) that enables the identification of the blade assembly including that insert 3. Identification of the blade assembly is, for example, performed by the power driver when the blade assembly is inserted into the driver's head in order to automatically verify that the blade that is being used is authentic and/or is adapted to a particular surgical procedure and/or to a particular driver.

Figure 7:
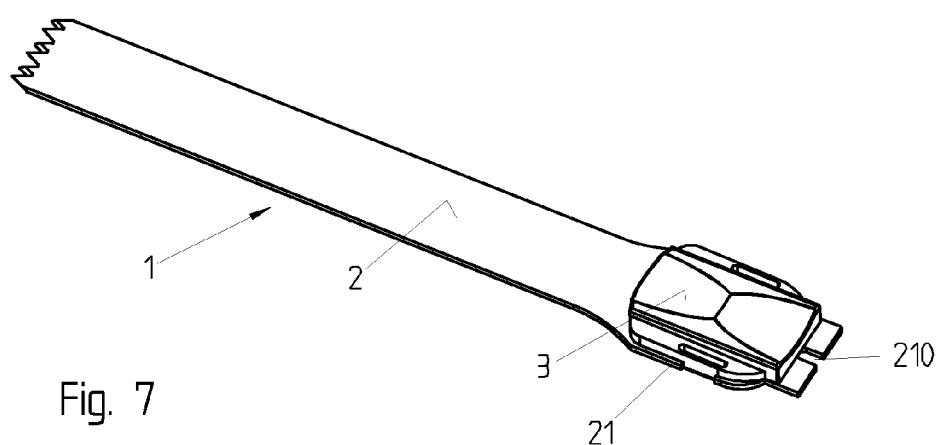
FIG. 7 is an illustrative example of an embodiment of a large blade assembly.

Large and/or long cutting blades exercise more vibration stress on the hand-piece and thus on the operator than small blades and there may be a need to have an integrated indicator on the blade itself and/or on the corresponding insert in order to allow larger and/or longer blades to function only with drills that have the necessary power for driving them during surgical operations. FIG. 7 shows an example of a blade assembly 1 having a large blade 2 with such an integrated indicator 210 or "key". In the illustrated example, the indicator 210 extends from the blade's distal end 21, beyond the insert 3. Heads of drivers that can drive such a long blade assembly 1 are then, for example, configured for accommodating the indicator 210 in a corresponding recess when the blade assembly 1 is inserted and locked on the driver's head, while heads of drivers that cannot safely drive such blades do not feature this recess, thereby preventing the insertion and locking of the large blade assembly 2.

In the illustrated embodiment, the constant dimension "b" of the blade assembly 1 that allows its use with a particular driver's head, is measured between a surface of the blade 2 to an opposite surface of the insert 3. Other configurations are however possible. According to variant embodiments, for example, the insert 3 surrounds the distal end of the saw blade on several sides, at least on its upper and lower sides, such that the constant dimension is measured from one surface of the insert to another side of the insert. According to these embodiments, the insert for example includes a slot or opening for receiving the distal end of the saw blade, and/or is made of two pieces that are affixed/attached on both opposite sides of the blade.

Thus, it is seen that devices, systems, and methods are presented in the subject disclosure. Although particular embodiments have been disclosed herein in detail, this has been done by way of example for purposes of illustration only, and is not intended to be limiting with respect to a claim or to any such embodiment. In particular, it is contemplated by the applicant that various substitutions, alterations, and modifications may be made without departing from the spirit and scope of the embodiments of the invention disclosed herein, and those of the exemplary claims which follow. Other aspects, advantages, and modifications are considered to be within the scope of the embodiments of the present disclosure.

REFERENCE NUMERALS 1 saw blade assembly
2 saw blade
20 aperture
21 proximal end 210 indicator
22 distal end
220 cutting portion
3 insert (or adapter)
30 lateral guide
31 clip
35 nib
36 opening
37 corner
38 lower side (of the insert 3)
4 head
40 locking pin
41 button
42 recess
a thickness (of the blade)
b constant dimension

We claim:

1. A kit of surgical blade assemblies, the kit comprising:
a plurality of blade assemblies configured and arranged for use with a driver for forming a surgical cutting tool, each surgical blade assembly of said plurality of surgical blade assemblies including:
a blade having a proximal end and a distal end, said distal end comprising a cutting portion, said proximal end having a thickness (a) which is less than what is applicable for use with a head of the driver; and
an insert having a longitudinal axis extending parallel to a longitudinal axis of the blade assembly, a first end, a second end, an upper surface extending between the first end and the second end, a lower surface extending between the first end and the second end, a first lateral side, and a second lateral side opposite the first lateral side, the first and second lateral sides extending between the upper surface and the lower surface and between the first end and the second end in a direction generally parallel to the thickness of the blade and parallel to the longitudinal axis of the insert, the insert affixed to the proximal end of said blade with the first end oriented towards the distal end of the blade, wherein the insert includes first and second nibs protruding outwardly in opposite directions from the first and second lateral sides of the insert, respectively, wherein each of the first and second nibs defines three lateral sides of an opening with a fourth lateral side of the opening defined by the corresponding lateral side of the insert such that each opening is enclosed on four lateral sides, wherein each of the first and second nibs is configured for being received by a corresponding recess in the head of the driver, and wherein the first and second nibs are insertable into the recesses in a direction parallel to the longitudinal axis of the blade assembly;
wherein said insert, when affixed to the proximal end of the blade, is configured and arranged to provide said blade assembly with at least one constant thickness (b) of a part of said blade assembly, said at least one constant thickness being measured from one surface of said saw blade to an opposite surface of said insert, to enable said blade to be used with the head of said driver, and wherein said constant thickness (b) allows a tight fit of said blade assembly in the corresponding driver's head with said blade in direct contact with said driver's head; and
wherein said blades of said plurality of surgical blade assemblies have different thicknesses (a) and said inserts of said plurality of surgical blade assemblies are configured and arranged such that said at least one constant thickness (b) is the same for all of said plurality of blade assemblies independently of the different blade thicknesses (a).

2. A kit of surgical blade assemblies according to claim 1, wherein said insert of each surgical blade assembly of said plurality of surgical blade assemblies comprises fastening means for affixing said insert to said proximal end of said blade of said blade assembly.

3. A kit of surgical blade assemblies according to claim 2, wherein said fastening means comprises clips.

4. A kit of surgical blade assemblies according to claim 1, wherein said insert of each blade assembly of said plurality of surgical blade assemblies is made of a plastic material.

5. A surgical cutting tool comprising:
a driver comprising a head, the head having first and second curved recesses;
a kit of surgical blade assemblies including:
a plurality of blade assemblies configured and arranged for use with the driver for forming a surgical cutting tool, each surgical blade assembly of said plurality of surgical blade assemblies including:
a blade having a proximal end and a distal end, said distal end comprising a cutting portion, said proximal end having a thickness (a) which is less than what is applicable for use with the head of the driver; and
an insert affixed to the proximal end of said blade, wherein the insert includes first and second nibs protruding outwardly in opposite directions from the insert, wherein each of the first and second nibs defines three lateral sides of an opening with a fourth lateral side of the opening defined by a lateral side of the insert such that each opening is enclosed on four lateral sides, wherein each of the first and second nibs includes a curved surface configured for being received by a corresponding one of the first and second curved recess in the head of the driver, and wherein the first and second nibs are insertable into the first and second recesses in a direction parallel to the longitudinal axis of the blade assembly;
wherein said insert, when affixed to the proximal end of the blade, is configured and arranged to provide said blade assembly with at least one constant thickness (b) of a part of said blade assembly, said at least one constant thickness being measured from one surface of said saw blade to an opposite surface of said insert, to enable said blade to be used with the head of said driver, and wherein said constant thickness (b) allows a tight fit of said blade assembly in the corresponding driver's head with said blade in direct contact with said driver's head; and
wherein said blades of said plurality of surgical blade assemblies have different thicknesses (a) and said inserts of said plurality of surgical blade assemblies are configured and arranged such that said at least one constant thickness (b) is the same for all of said plurality of blade assemblies independently of the different blade thicknesses (a); and
wherein the head of the driver is configured and arranged to receive any blade assembly of said plurality of blade assemblies,
wherein said blade is in tight and direct contact with said head when said blade assembly is locked onto said head.

6. A surgical cutting tool according to claim 5, wherein said head comprises a locking mechanism configured and arranged to removably lock said surgical blade assembly on said head.

7. A surgical cutting tool according to claim 6, wherein said locking mechanism comprises a tool-less mechanism.

8. A surgical cutting tool according to claim 7, wherein said locking mechanism comprises a self-locking pin.

9. Surgical cutting tool kit, comprising:

a driver comprising a head for receiving a blade assembly, the head having first and second recesses;

a kit of surgical blade assemblies configured and arranged to be used with said driver, the kit of surgical blade assemblies including:

a plurality of blade assemblies configured and arranged for use with the driver for forming a surgical cutting tool, each surgical blade assembly of said plurality of surgical blade assemblies including:

a blade having a proximal end and a distal end, said distal end comprising a cutting portion, said proximal end having a thickness (a) which is less than what is applicable for use with the head of the driver; and an insert having a longitudinal axis extending parallel to a longitudinal axis of the blade assembly, a first end, a second end, an upper surface extending between the first end and the second end, a lower surface extending between the first end and the second end, a first lateral side, and a second lateral side opposite the first lateral side, the first and second lateral sides extending between the upper surface and the lower surface and between the first end and the second end in a direction generally parallel to the thickness of the blade and parallel to the longitudinal axis of the insert, the insert affixed to the proximal end of said blade, wherein the insert includes first and second nibs protruding outwardly in opposite directions from the insert, wherein each of the first and second nibs defines three lateral sides of an opening with a fourth lateral side of the opening defined by a lateral side of the insert such that each opening is enclosed on four lateral sides, wherein each of the nibs is configured for being received by a corresponding one of the first and second recess in the head of the driver, and wherein the first and second nibs are insertable into the first and second recesses in a direction parallel to the longitudinal axis of the blade assembly;

wherein said insert, when affixed to the proximal end of the blade, is configured and arranged to provide said blade assembly with at least one constant thickness (b) of a part of said blade assembly, said at least one constant thickness being measured from one surface of said saw blade to an opposite surface of said insert, to enable said blade to be used with the head of said driver, and wherein said constant thickness (b) allows a tight fit of said blade assembly in the corresponding driver's head with said blade in direct contact with said driver's head; and wherein said blades of said plurality of surgical blade assemblies have different thicknesses (a) and said inserts of said plurality of surgical blade assemblies are configured and arranged so that said at least one constant thickness (b) is the same for all of said plurality of blade assemblies independently of the different blade thicknesses (a).

10. A surgical blade assembly for use with a driver having a head for driving the surgical blade assembly, comprising:

a blade having a proximal end and a distal end, said distal end comprising a cutting portion, said proximal end having a thickness; and an insert affixed to the proximal end of said blade and having a thickness greater than the thickness of the blade, the insert including first and second nibs protruding outwardly in opposite directions from the insert, the first and second nibs each including an opening disposed therein separating the first and second nibs from a body of the insert for at least a portion of a length of each of the first and second nibs, wherein each opening is surrounded and enclosed by the nib on three lateral sides and by the body of the insert on a fourth lateral side, wherein each of the first and second nibs is configured for being received by a corresponding recess in the head of the driver, and wherein the first and second nibs are insertable into the recesses in a direction parallel to the longitudinal axis of the blade assembly.

* * * * *